United States Patent [19]

Steer et al.

[11] 4,300,560
[45] Nov. 17, 1981

[54] OSTOMY BAG HAVING A BOTTOM DRAIN VALVE

[75] Inventors: Peter L. Steer; John V. Edwards, both of, East Grinstead, England

[73] Assignee: Kingsdown Medical Consultants, Ltd., London, England

[21] Appl. No.: 129,147

[22] Filed: Mar. 10, 1980

[30] Foreign Application Priority Data

Aug. 6, 1979 [GB] United Kingdom ............. 7927295

[51] Int. Cl.³ ............................................. A61F 5/44
[52] U.S. Cl. ............................................. 128/283
[58] Field of Search ................... 128/760–762, 128/767, 275, 283, 294, 295, 272, DIG. 24; 150/6–8, 44; 215/355, DIG. 3; 222/528–531, 537

[56] References Cited

U.S. PATENT DOCUMENTS

| | | | |
|---|---|---|---|
| 3,205,889 | 9/1965 | Alder et al. | 128/272 |
| 3,292,626 | 12/1966 | Schneider | 128/295 |
| 3,529,599 | 9/1970 | Folkman et al. | 128/272 |
| 3,532,092 | 10/1970 | Rodgers | 128/283 |
| 3,780,739 | 12/1973 | Frank | 128/283 |
| 4,023,607 | 5/1977 | Jensen et al. | 150/1 |
| 4,054,140 | 10/1977 | Estes | 128/283 |
| 4,078,568 | 3/1978 | Estes et al. | 128/283 |
| 4,084,590 | 4/1978 | Caraway et al. | 128/283 |
| 4,085,752 | 4/1978 | Canale | 128/283 |
| 4,106,507 | 8/1978 | Kellermeyer et al. | 128/295 |
| 4,191,231 | 3/1980 | Winchell et al. | 150/8 |

FOREIGN PATENT DOCUMENTS

| | | |
|---|---|---|
| 732155 | 6/1955 | United Kingdom . |
| 743535 | 1/1956 | United Kingdom . |
| 827874 | 2/1960 | United Kingdom . |
| 890018 | 2/1962 | United Kingdom . |
| 1024661 | 3/1966 | United Kingdom . |
| 1128186 | 9/1968 | United Kingdom . |

*Primary Examiner*—C. Fred Rosenbaum
*Attorney, Agent, or Firm*—Lawrence S. Levinson; Stephen B. Davis

[57] ABSTRACT

An ostomy bag having a drain valve at a lower region thereof. The valve is formed of a short flexible tube that can be bent or kinked over a support web and a stopper which can be pushed into the open end of the kinked tube.

9 Claims, 6 Drawing Figures

OSTOMY BAG HAVING A BOTTOM DRAIN VALVE

BACKGROUND OF THE INVENTION

The construction of a stoma, or ostomy, an artificial opening of the intestinal or urinary tract to the abdominal wall, has been developed as a technique to provide both cure and palliation for benign and malignant diseases. A urinary conduit is constructed to compensate for the loss of or severe malfunction of the urinary bladder. Construction of the stoma involves isolation of a segment of small intestine and the restriction of continuity of the remainder of the small intestine. One end of the segment is brought to the abdominal wall as a stoma while the other end is closed. The ureters are implanted in the segment to allow free passage of urine to the exterior of the body.

In order to collect the urine which is discharged from the stoma, a bag or pouch is affixed to the body around the stoma. The bag includes means to drain the contents without the need for removing the bag from the body.

SUMMARY OF THE INVENTION

This invention is directed to an ostomy bag having a drain valve at the bottom and a method of making such a bag. The valve assembly includes a short flexible tube that can be bent or kinked to cut off flow and a tube securing means for temporarily holding the tube in its kinked condition.

According to a preferred aspect of the invention, the short flexible tube is molded integrally with a plastics connecting plate which is welded to the lower edges of the front and rear bag walls. The tube may project normally upwardly and downwardly from respective upper and lower surfaces of the plate, and the plate may include first and second integral webs which extend from the plate respectively to the projecting upper and lower portions of the tube. The purpose of the first web is to stiffen the root portion of the tube and ensure that the kinking occurs at an appropriate place along the length of the tube so as to reduce the chance of leakage past the kink. The purpose of the second wed is to provide some longitudinal stiffness in the connecting plate so that it can more readily be aligned with the edges of the bag walls for the welding operation.

The ostomy bag of this invention is particularly adapted to collect urine discharged from a stoma. The bag includes front and rear walls secured together around their pheriphery. The rear wall has an orifice surrounded by a coupling member. The bag preferably also includes a pair of intermediate walls one of which is secured around the orifice and is secured in face-to-face relationship to the other wall of the pair at spaced zones near to the lower edges of their intermediate walls located below the orifice. With such an arrangement, the marginal surfaces of the intermediate walls between the zones where they are secured together tend to lie against one another, and in effect form a parallel series of non-return flap valves, allowing passage of urine from an upper or "first" space in the bag located between the intermediate walls and in communication with the orifice to a lower or "second" space in the bag located between the front and rear walls, and substantially preventing passage of urine back into the first space even when the bag is subjected to accidental impacts or pressure. It will be realized that with this construction the space defined between the front wall and the front one of the intermediate walls is in unrestricted communication with the second space and serves as a space into which the urine can flow if the lower part of the bag is compressed, without, however, allowing the urine to reach the orifice and contact the skin of the wearer of the bag.

In this specification, the words "front" and "rear" respectively mean the wall of the bag further from and nearer to the body of the wearer when the bag is in normal use position.

DETAILED DESCRIPTION OF THE INVENTION

Figure 1:
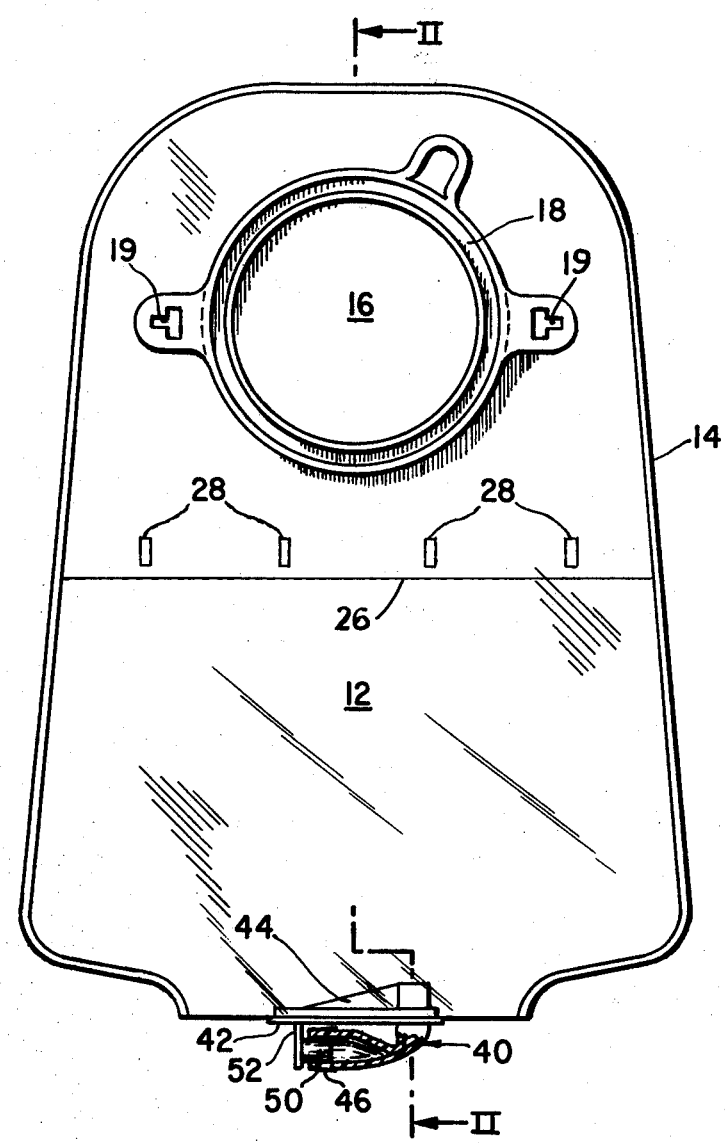
FIG. 1 is an elevation view of the rear of a bag according to one embodiment of the invention.
Figure 2:
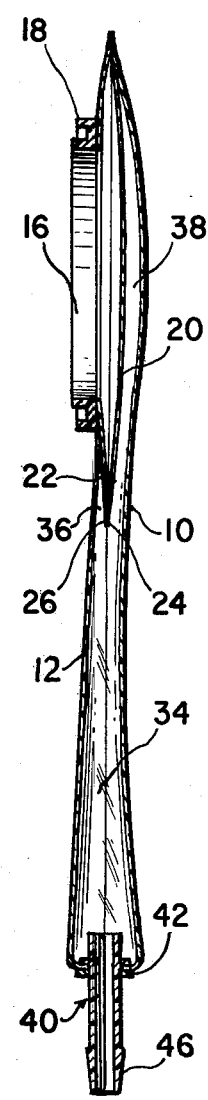
FIG. 2 is a partial section on the line II—II in FIG. 1, but showing the drain valve tube in its "down" i.e., open position and omitting the stoppers.

The bag shown in FIGS. 1 and 2 has a front wall 10 and a rear wall 12 of a synthetic plastics material which may for example be transparent. These walls 10 and 12 are secured together by a heat weld 14 around their periphery so producing a substantially flat bag. The rear wall has an orifice 16 through which the stoma protrudes. A channel shaped coupling member 18 is affixed around the periphery of orifice 16. The coupling member 18 attaches the bag to a second coupling affixed to the body around the stoma. This coupling system is disclosed and claimed in copending application U.S. Ser. No. 881,274 filed Feb. 27, 1978. The coupling member 18 also includes openings 19 for the optional attachment of a belt to aid in securing the bag to the body.

The bag includes a front intermediate wall 20 and a rear intermediate wall 22 which are sealed at their edges to the other walls by the heat weld 14, and are both located parallel to the walls 10 and 12 when the bag is flat. The intermediate walls 20 and 22 extend part-way down the height of the bag, and are free of attachment to the front and rear walls 10, 12 along their lower edges 24, 26. The lower edges 24, 26 are in practice located about 20 millimeters. below the bottom of the orifice 16. The intermediate walls 20 and 22 are welded to each other at four spaced zones 28 linearly arranged across the bag. Between these zones the walls 20 and 22 are not connected to each other. In use, urine discharged into the bag enters first the space between the walls 20 and 22 and then falls down the spaces between the welded portions into the space 34 between the lower portions of the walls 10 and 12. If then the bag is accidentally struck or squeezed, the urine will tend to move upwardly into the regions 36 and 38 (FIG. 2) and will be kept away from the orifice 16, so reducing the discomfort to the wearer and the risk of escape of liquid.

According to a first embodiment of the invention, the drain valve located at the bottom of the bag consists of a short flexible tube 40 (FIGS. 1 and 2) which is molded integral and with a flexible mounting plate 42. The plate 42 and tube 40 are both preferably made of synthetic plastics material. The tube 40 has an upper portion within the bag which is integral with a reinforcing rib 44 also connected to the plate 42. The tube also has a lower portion 46 which can be bent through approximately 90° as indicated in FIG. 1 (or through an obtuse angle in other embodiments, as may be necessary in order to fully close the tube). Such a bending closes off the tube and provides the closed condition of the valve.

The tube securing means is formed by a stopper 50 connected by a connecting tab 52 to the mounting plate 42. The positioning is such that the stopper 50 can readily be placed in the end of the bent tube as seen in FIG. 1. It is an advantageous feature of this invention that the tube 40, the plate 42, the rib 44, the tab 52 and stopper 50 are all molded as a single part, for example of ethylene vinyl acetate (e.v.a), in a single molding operation. Also this part is readily secured to a lower region of the bag by a single heat welding operation. The wall of the tube 40 is preferably thin. For example it may have a wall thickness of one-half millimeter of less. This feature is of value in ensuring that the kinking of the tube collapses it so that its opposite walls touch, thereby closing off the through passage.

Such a construction of a bag and drain valve enables an extremely light product to be made, and use of the valve is simple and does not require two hands. The bag and valve are comfortable for a wearer.

Figure 3:
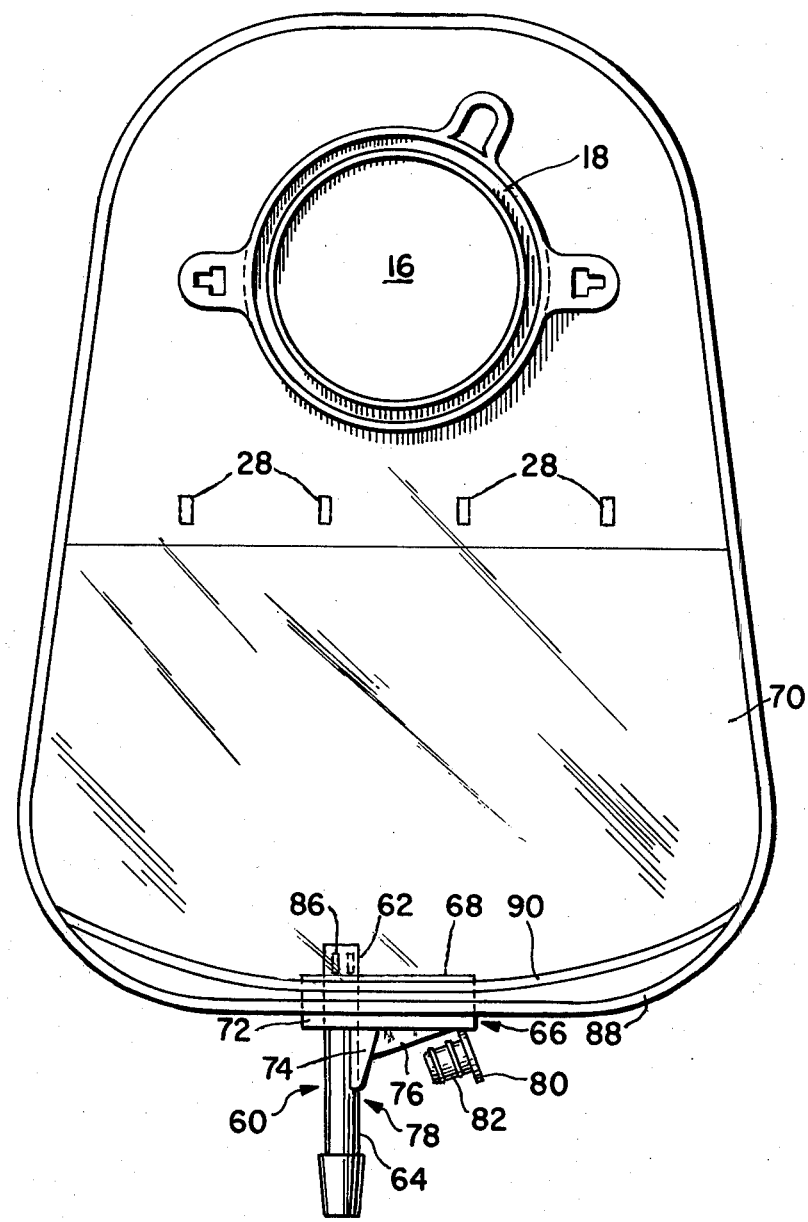
FIG. 3 is a front elevation of a second embodiment of the invention.

In an alternative embodiment of the invention, illustrated in FIG. 3, the tube 60 has upper and lower portions 62, 64 and the plastic mounting or connecting plate 66 is inverted T-shaped in cross-section having an upstanding web 68 which is welded to the lower regions of the bag walls 70 and a flat block portion 72 through which the tube 60 passes. A support web 74 is integral with the block 72 and the lower portion of the tube 64, and this web 74 is connected to the block portion 72 by a thin web 76. This construction serves to ensure that kinking of the lower portion 64 of the tube occurs always in the region 78. An integral tab 80 and stopper 82 are attached at the other end of the block 72 in a similar way to the embodiment of FIGS. 1 and 2.

The upper portion 62 of the tube has holes 86 therein, and the bag front and rear wall are welded together by two welds, one weld 88 which secures the bag walls to a lower part of the upstanding web 68 and a second weld 90 which secures them to an upper part of the web 68. The holes 86 are located above the upper weld 90. This arrangement is to ensure that all collected urine can drain away and to avoid collection of static pockets of fluid.

Figure 4:
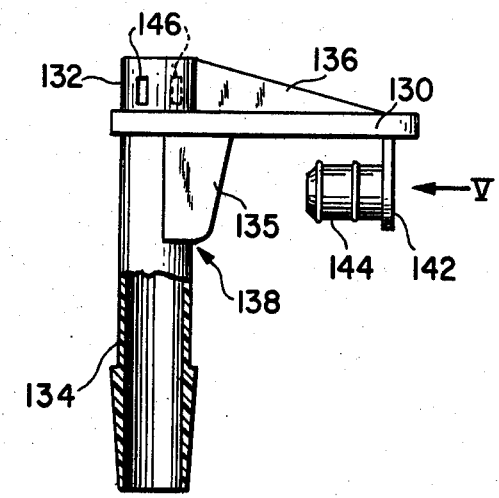
FIG. 4 is a front elevation of a third embodiment of the invention looking in the direction IV in FIG. 5.
Figure 5:
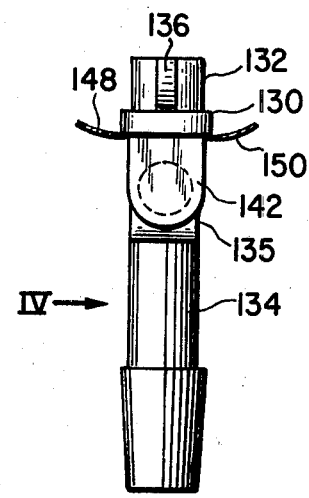
FIG. 5 is an end elevation looking in the direction V in FIG. 4.

Another form of drain tube assembly is shown in FIGS. 4 and 5. A plastics connecting plate 130 is molded integral with upper and lower drain tube portions 132 and 134. An integral vertical web 136 connects the upper portion 132 to the plate, and an integral support block 135 connects the lower portion to the plate so ensuring that the tube kinks at the region 138. An integral tab 142 carries a stopper 144. The tube portion 132 has holes 146 therein. It will be seen that plate 130 extends laterally outwardly and bag walls 148 and 150 are shown in FIG. 5 welded to the plate 130. This form of drain tube assembly can be used in making an ostomy bag in the manner described below in connection with FIG. 6.

Figure 6:
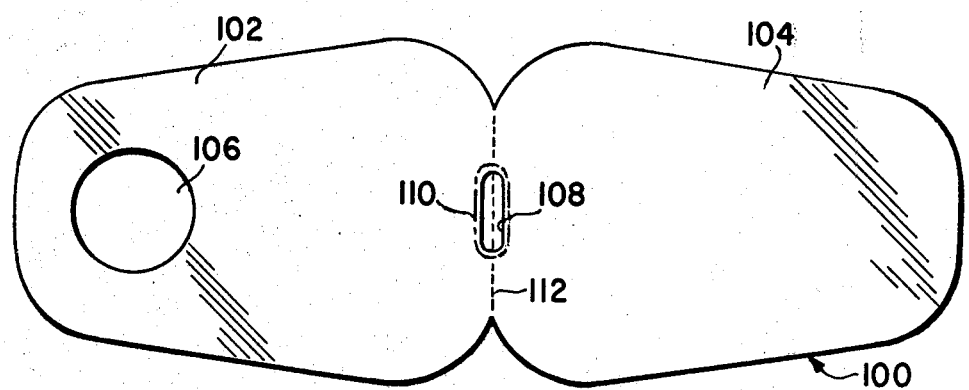
FIG. 6 illustrates a method of making a bag according to the invention.

The drainable bags of this invention can be made by two alternate methods. In the first method, the two bag walls are separately cut to shape and are welded one to each side of a thin vertical web (web 68 in FIG. 3). In the other method, a single sheet of plastics material is cut in the shape of two lobes which when folded over at their join and welded around their edges to form the bag, with this method a hole is punched or cut at the approximate mid-point of the fold-line. This is illustrated in FIG. 6. A sheet of plastics 100 is cut in the form of two lobes 102, 104. A hole 106 for the bag coupling is punched in the lobe 102, together with a second hole 108 to receive the plastics connecting plate carrying the drain tube. The latter is welded to the sheet 100 around the weld line 110 indicated by the chain-dotted line, and then one lobe is folded over onto the other, the fold line being shown by the dotted line 112.

The two lobes 102 and 104 then constitute the rear and front bag walls, and after insertion of the intermediate layers referred to above, are welded together around their periphery in order to form a completed bag.

What is claimed is:

1. An ostomy bag having front and rear walls of synthetic plastics material sealed to each other around their periphery, an opening in said rear wall for passage of the stoma, and a drain valve secured in an opening at the lower region of said bag, said valve comprising a mounting plate having a tube passing therethrough, a stopper dimensioned to fit in said tube and connected by a tab to the bottom of said mounting plate, and a support web extending from the bottom of said mounting plate to a portion of said tube below said mounting plate whereby the lower portion of said tube is bent over said support web and sealed by said stopper.

2. A bag according to claim 1 in which the tube, the mounting plate, the support web, and the stopper and tab are all made in one piece from plastics material.

3. A bag according to claim 2 in which the plastics material is ethylene vinyl acetate.

4. A bag according to claim 3 in which there is at least one intermediate wall positioned to avoid splash-back of liquid contents of the bag into an upper region of the bag.

5. A bag according to claim 4 in which a channel-shaped coupling member is affixed around the periphery of the stoma opening in the rear bag wall.

6. A bag according to claim 2 in which the mounting plate has two opposed faces which are secured in a face-to-face manner to adjacent regions of the front and rear bag walls.

7. A bag according to claim 2 in which a second web extends from said mounting plate to the upper portion of said tube.

8. A bag according to claim 2 in which the mounting plate has an annular surface which is secured in face-to-face relationship with a confronting edge strip of a single sheet of plastics material that had been folded over and which when welded around its edges forms the bag.

9. A method of making an ostomy bag comprising:
(a) cutting a coupling hole and a drain tube hole in a single sheet of plastics material,
(b) welding a drain tube assembly to the edge of the drain tube hole and a coupling member to the edge of the coupling hole said drain tube assembly comprising a mounting plate through which a short flexible tube passes, a support web extending from the bottom surface of said mounting plate to a part of the lower wall of said tube, and a stopper dimensioned to fit in the tube free end and connected to the mounting plate by a tab, (c) folding the sheet over along an intermediate line which intersects the drain tube assembly, (d) interposing a pair of intermediate sheets of plastics material between the lobes of the folded sheet, and (e) welding the periphery of the folded sheets so as to weld the intermediate sheets in place and form a completed bag.

* * * * *